United States Patent
Mele et al.

(10) Patent No.: US 11,951,296 B2
(45) Date of Patent: Apr. 9, 2024

(54) DEVICE FOR THE VENTRICULAR EMERGENCY SUPPORT

(71) Applicants: Giuseppe Mele, Rome (IT); Marco Mele, Rome (IT); Armando Bonavoglia, London (GB); Valentina Liuzzi, Rome (IT)

(72) Inventors: Giuseppe Mele, Rome (IT); Marco Mele, Rome (IT)

(73) Assignee: MLB INNOVATION SRL, Rome (IT)

(*) Notice: Subject to any disclaimer, the term of this patent is extended or adjusted under 35 U.S.C. 154(b) by 0 days.

(21) Appl. No.: 17/253,683

(22) PCT Filed: Jun. 18, 2019

(86) PCT No.: PCT/IT2019/000050
§ 371 (c)(1),
(2) Date: Dec. 18, 2020

(87) PCT Pub. No.: WO2019/244180
PCT Pub. Date: Dec. 26, 2019

(65) Prior Publication Data
US 2021/0187271 A1    Jun. 24, 2021

(30) Foreign Application Priority Data
Jun. 21, 2018  (IT) .......... 102018000006538

(51) Int. Cl.
*A61M 60/157* (2021.01)
*A61M 60/139* (2021.01)
(Continued)

(52) U.S. Cl.
CPC ........ *A61M 60/157* (2021.01); *A61M 60/139* (2021.01); *A61M 60/295* (2021.01);
(Continued)

(58) Field of Classification Search
CPC .......... A61M 60/165; A61M 60/497
See application file for complete search history.

(56) References Cited

U.S. PATENT DOCUMENTS 4,546,759 A    10/1985  Solar
6,071,271 A *  6/2000  Baker ............... A61M 25/1011
                                                          604/523

(Continued)

FOREIGN PATENT DOCUMENTS

WO    03068292 A1    8/2003
WO    03068303 A2    8/2003

*Primary Examiner* — Rex R Holmes
*Assistant Examiner* — Jennifer L Ghand
(74) *Attorney, Agent, or Firm* — David Guerra

(57) ABSTRACT

The present invention concerns a device for the ventricular emergency support, comprising: a first flexible catheter (2), with a variable transversal section, provided with an extremal balloon (7) for the controlled occlusion of the ascending aorta (AA) of the treated patient; a first pump (12), associated to said first catheter (2) for the aspiration and contemporary input of equivalent blood quantifies into the blood circle of the treated patient; a second flexible catheter (32), with a fixed transversal section, provided with a couple of extremal balloons (34), spaced apart, for the controlled occlusion of the inferior vena cava (CA) and of the superior vena cava (CD) of the treated patient; a second pump (35), associated to said first and second catheter (2, 32) for inflating and deflating said extremal balloons (7, 34) of said first and second catheter (2, 32); an electronic control unit (36) for adjusting and controlling the operational parameters of said first and second pump (12, 35), and for the detection of the cardiac parameters of the treated patient; rechargeable or network means (37, 38) for the power supply of above mentioned components.

20 Claims, 3 Drawing Sheets

(51) Int. Cl.
*A61M 60/295* (2021.01)
*A61M 60/497* (2021.01)
*A61M 60/515* (2021.01)
*A61M 60/569* (2021.01)
*A61M 60/843* (2021.01)
*A61M 60/857* (2021.01)
*A61M 60/873* (2021.01)
*A61M 60/876* (2021.01)
*A61M 60/892* (2021.01)

(52) U.S. Cl.
CPC ........ *A61M 60/497* (2021.01); *A61M 60/515* (2021.01); *A61M 60/569* (2021.01); *A61M 60/843* (2021.01); *A61M 60/857* (2021.01); *A61M 60/873* (2021.01); *A61M 60/876* (2021.01); *A61M 60/892* (2021.01); *A61M 2205/0216* (2013.01); *A61M 2205/3375* (2013.01)

(56) References Cited

U.S. PATENT DOCUMENTS

| | | | |
|---|---|---|---|
| 6,241,699 B1 | 6/2001 | Suresh | |
| 6,508,777 B1 * | 1/2003 | Macoviak | A61M 1/3659 604/9 |
| 6,726,651 B1 * | 4/2004 | Robinson | A61M 1/3613 604/4.01 |
| 2003/0191448 A1 * | 10/2003 | Swindle | A61M 25/1011 604/509 |
| 2016/0263356 A1 * | 9/2016 | Selim | A61M 1/3666 |

* cited by examiner

DEVICE FOR THE VENTRICULAR EMERGENCY SUPPORT

The present invention concerns the technical sector of the ventricular assist cardiac equipments (VAD, ventricular assist device).

More in detail, the present invention concerns a device for the ventricular emergency support that may be reversibly applicable to an individual with heart attack so as to guarantee blood circulation also with a heart damaged or under arrest.

Cardiac infarction (heart attack—or acute myocardial infarction) defines the functional crisis of the heart due to the interruption of the local blood circulation produced by the occlusion of one or more coronary vessels.

The infarction triggers the general suffering and the potential occurrence of serious functional deficiencies in those parts of the heart which are no longer correctly supplied with the local blood circulation and a following insufficient blood circulation in the large systemic circle as well as in the small pulmonary circle.

The death risk for the individual caught by heart attack therefore depends on the insufficient blood circulation produced by the suffering heart, which unavoidably slows down its action of pumping the blood until it definitely stops in the most serious cases.

The extreme and sudden debilitation of the individual caught by heart attack determines the further complication of hindering and making very risky the rapid execution of analysis operations (like coronary angiography) and/or the treatment of the heart problems (coronary angioplasty etc.), as said interventions are performed with invasive techniques, which are often difficult to bear by an individual in cardiac distress.

It is the aim of the present invention to propose a device for the ventricular emergency support able to help or replace the heart it its natural function of pumping the blood, so as to restore the health conditions of an individual caught by heart attack to a situation allowing sufficient medical control in quick times and consequently make possible the rapid treatment with the analysis and intervention techniques usually provided, and therefore the drastic reduction of the death risk.

The aim set forth is reached by means of a device for the ventricular emergency support according to the main independent claim 1.

Further features of the present invention are described in the dependent claims.

The device for the ventricular emergency support according to the present invention produces many and important advantages, as:

- in case of heart damaged or under arrest due to infarction, it allows to assist or replace the function of pumping the blood normally guaranteed by the left heart ventricle;
- supporting or replacing the left heart ventricle, it determines the reduction of the afterload of said ventricle with the following reduction of the myocardial consumption of molecular oxygen ($O_2$);
- in case of a heart damaged or under arrest due to infarction, it allows to assist or replace the function of pumping the blood normally guaranteed by the right heart ventricle;
- assisting or replacing the right heart ventricle, it determines the recall of blood from the periphery and its flow into the pulmonary circle;
- it allows its connection to the large vessels of the large circle (aorta and venae cavae, hollow veins) of the individual caught by infarction through the inguinal tracts of the arteries of the femoral veins, with the sole ultrasound or optical assistance;
- it allows a quick stabilization of the blood circulation of the individual caught by infarction and consequently a rapid treatment with the known analysis techniques (coronary angiography) and/or intervention (coronary angioplasty etc.);
- it allows a drastic reduction of the death risk for the individual caught by infarction;
- it allows to greatly improve the functions of ventricular assistance currently provided by IABP (Intra Aortic Balloon Pump) devices;
- it allows, in many cases, to replace the functions of ventricular assistance actually provided by VAD (Ventricular Assist Device) devices to surgical implant or to extracorporeal circulation machines (heart-lung etc.).

Further features and advantages of the device according to the present invention will be more evident from the following detailed description relating to the enclosed drawings, in which a preferred embodiment is shown for exemplifying and not limiting purposes, in which.

Figure 1:
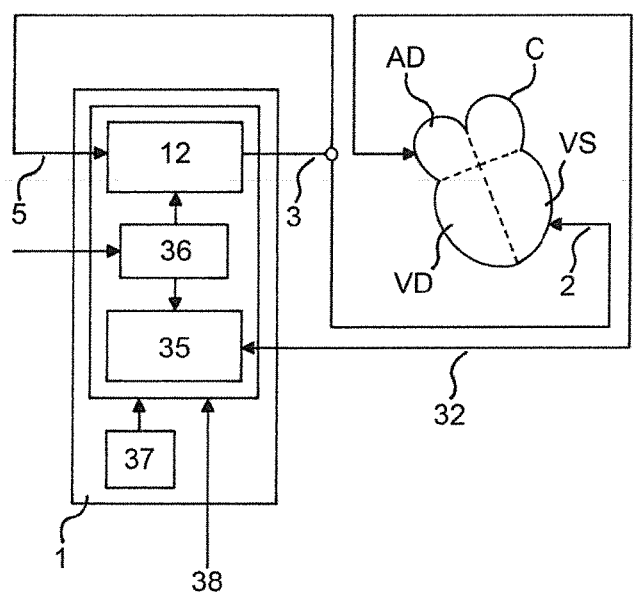
FIG. 1 shows a scheme of the structural conformation and the general working principle of a device for the ventricular emergency support according to the present invention.

Relating now to the details of the FIGS. 1, 5, 6, 7, 8, a device for the ventricular emergency support (1) according to the present invention mainly comprises:

- a first flexible catheter 2, with a variable transversal section, provided with a small extremal balloon 7 capable of determining the controlled occlusion of the ascending aorta AA of the treated patient;
- a first blood circulation pump 12, associated to said first catheter 2 for the aspiration and contemporary input of equivalent blood quantities into the blood circle of the treated patient, in synchrony with the heart rhythm of said patient;
- a second flexible catheter 32, with a fixed transversal section, provided with a couple of extremal small balloons 34, slightly spaced apart, for the controlled occlusion of the inferior vena cava CA and of the superior vena cava CD of the patient treated;
- a second pump 35, associated to said first and second catheter 2, 32 for the cyclic inflating and deflating of extremal small balloons 7, 34 of said first and second catheter 2, 32, in synchrony with the heart rhythm of the patient treated;
- an electronic control unit 36 for adjusting and controlling the operational parameters of said first and second pump 12, 35, and for the detection of the cardiac parameters of the treated patient;
- rechargeable or network means 37, 38 for the power supply of the above mentioned components.

Relating to the details of FIGS. 1, 3, 4, 5, 6, the first catheter 2 comprises:

- an elastic duct 3 for the inlet of blood into the blood flow of the treated patient, connected to the outlet duct of said first pump 12, able to vary the amplitude of its own transversal section in proportion to the quantity and to the pressure of the blood introduced in the blood flow of the patient:
- a containment sleeve 4, integrated in said elastic duct 3, for defining the greatest amplitude reachable by the transversal section of said elastic duct;

a non-collapsible duct 5, internal to said elastic duct 3, for the blood aspiration from the blood flow of the treated patient, connected to the inlet duct of said first pump 12;

a capillary duct 6, internal to said non-collapsible duct 5 for inflating and deflating said extremal small balloon 7, connected to said second pump 35.

The first catheter 2 can be inserted into the inguinal tract of the femoral artery AF and traced backwards in the blood circle of the patient treated until it has reached the ascending aorta AA, so as to determine the temporary occlusion thereof by inflating and deflating the relative extremal small balloon 7.

The extremal small balloon 7 of the first catheter 2 has, in its inflated condition, an indicatively umbrella-shaped form and comprises a light 8 for the passage of the blood aspired by the blood flow of the patient treated through the non collapsible duct 5 of said first catheter 2 connected to the inlet duct of the first pump 12, and shaped loops 9 for the reflux of the blood introduced into the blood flow of the patient treated through elastic duct 3 of said first catheter 2 connected to the outlet duct of the first pump 12.

Figure 9:
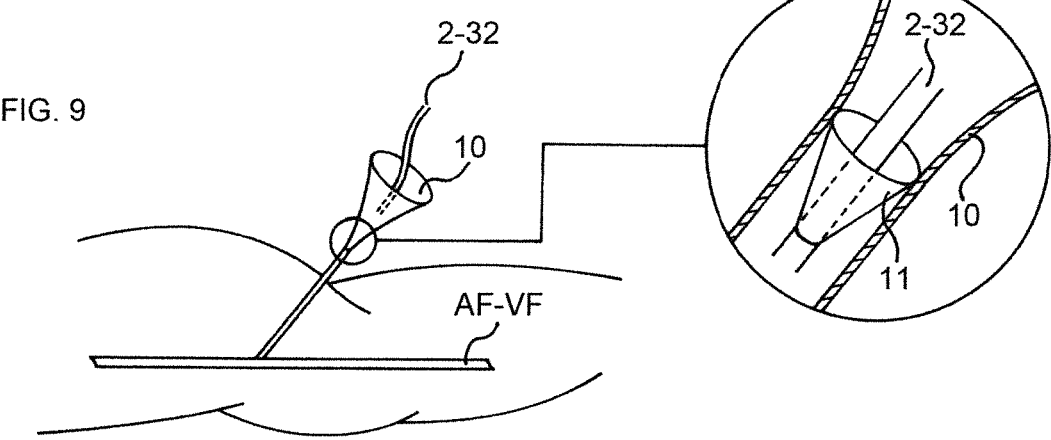

As shown in FIG. 9, the first catheter 2 is introduced into the inguinal tract into the femoral artery AF by means of a needle introducer 10 provided with an elastic sealing valve 11 that automatically adapts to the transversal section of the elastic duct 3 of said catheter so as to avoid possible blood leaks form the blood circle of the patient.

Figure 2:
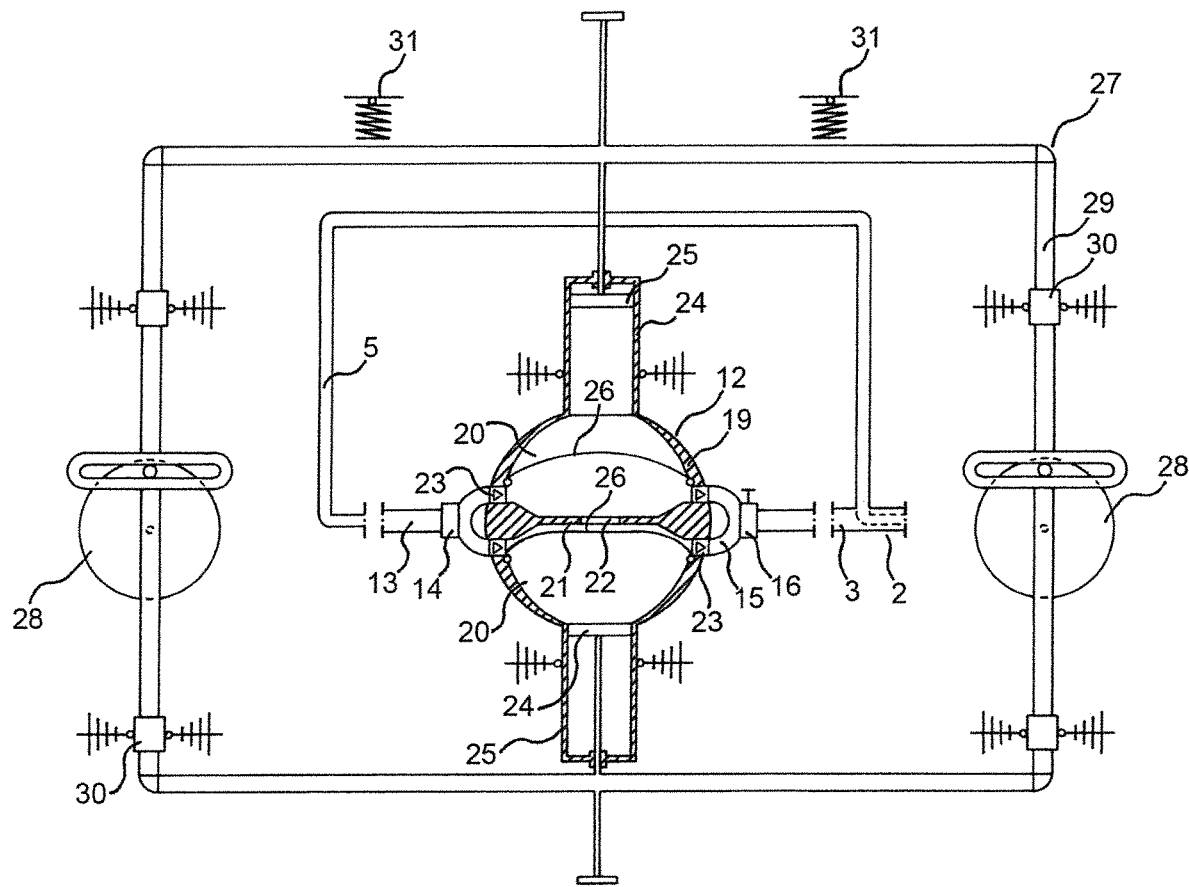
FIGS. 2, 3, 4, 5, 6, 7, 8, 9 show in a scheme the realization details and the operating phases of said device.

Relating to the details of FIG. 2, the first pump 12 for blood circulation associated to the first catheter 2 comprises:

a y-shaped duct 13, for the inlet of the blood aspired from the blood flow of the treated patient, provided with an electrovalve 14, connected to the non-collapsible duct 5 of the first catheter 2;

a y-shaped duct 15, for the outlet of the blood inserted into the blood flow of the treated patient, provided with an electrovalve 16, connected to the elastic duct 3 of the first catheter 2;

an approximately spherical machine body 19, containing two internal chambers 20, separated by a rigid median septum 21 provided with an electrovalve 22, connected to ducts 13, 15 by means of unidirectional valves 23, working by difference of pressure, imposing to the blood entering and leaving said internal chambers 20 to always move in the same direction;

two hydraulic cylinders 24 with relative pistons 25 that cyclically manage the compression and expansion of an operating fluid, kept separate from the blood contained in the internal chambers 20 by means of elastic membranes 26;

an electromechanical mechanism 27 for operating pistons 25 of the hydraulic cylinders 24, provided with eccentric kinematic mechanism 28 associated to a frame 29 integral with said pistons 25 and linearly sliding on guides 30 with a stroke limited by cushioning springs 31.

The kinematisms 28 of mechanism 27 for operating pistons 25 support adjustments that may influence the speed and width of the race inside said hydraulic cylinders 24 associated to the internal chambers 20 of the first pump 12 for the blood circulation. The speed of pistons 25 inside hydraulic cylinders 24 defines in fact the advancement speed of the blood in inlet and outlet ducts 13, 15 from internal chambers 20 of pump 12, while the excursion of the race of pistons 25 in hydraulic cylinders 24 defines the quantity of blood moved through said ducts 13, 15 so as to determine the pressure value imposed to the blood circle of the patient treated.

Furthermore, the internal components of pump 12 placed into direct contact with the treated patient's blood have dimensional and structural features such as to limit their interference with the blood circle and the relative corpuscles (globules, platelets etc.) and consequently the risks of outbreaks of thrombi or emboli in the patient himself.

Figure 7:
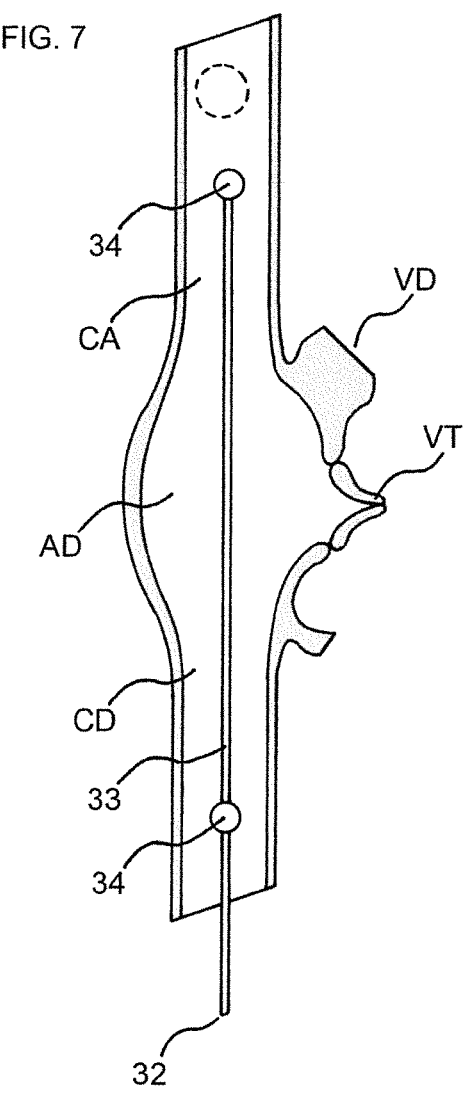
Figure 8:
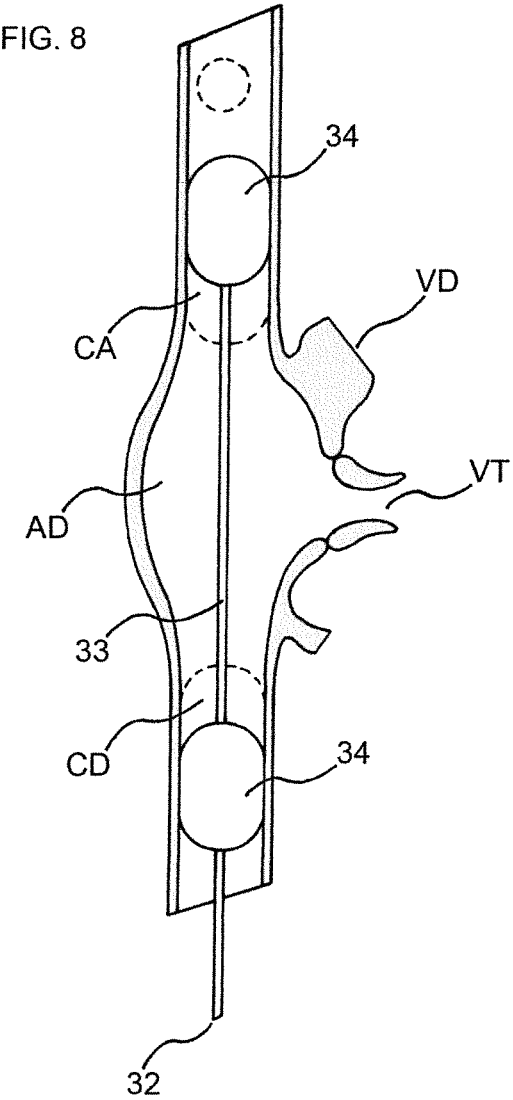

Relating to the details of FIGS. 7, 8, the second catheter comprises a single non-collapsible duct 33 for inflating and deflating the extremal balloons 34 connected to the second pump 35.

The second catheter 32 may be introduced into the inguinal tract of femoral vein VF and traced back along the bloodstream of the treated patient until it reaches the area of the right cardiac ventricle VD comprised between the inferior vena cava CA and the superior vena cava CD so as to determine the temporary occlusion thereof by means of cyclic inflating and deflating of both extremal balloons 34.

Extremal balloons 34 of the second catheter 32 initially have an indicatively spherical shape that expands in preshaped way in direction of the right heart atrium AD due to the inflating action on them by second pump 35.

The extremal balloons 34 of the second catheter 32 are spaced apart so as to get placed respectively between the right heart atrium AD and the first branch of the inferior vena cava CA and in the part of the superior vena cava CD near to heart C of the treated patient.

As shown in FIG. 9, the second catheter is introduced in the inguinal tract of femoral vein VF through the same needle introducer 10 with sealing elastic valve 11 that may be used with first catheter 2 or by means of a standard needle introducer.

As shown in FIGS. 5, 6, 7, 8 first catheter 2 and second catheter 32 and relative extremal balloons 7, 34 have smooth, soft surfaces without sharp edges so as to avoid damages to the tissues of the arterial or venous vessels and forms and dimensions for limiting the interferences with the blood circle and the relative particles (globules, platelets etc.) and consequently the risk of outbreaks of thrombi or emboli in the patient.

Furthermore, the distal ends of the first and second catheter 2, 32 are out of materials suitable for allowing its ultrasound detection or comprise fragments of such materials inside.

The electronic control unit 36, that may be manually operated by health workers, comprises means for adjusting and controlling the operative parameters of first pump 12 for the blood circulation and of the second pump 35 for the cyclic inflating and deflating of extremal balloons 7, 34 of catheters 2, 32, and for the detection of cardiac parameters of the treated patient, to perform the following functions:

controlling the electrovalves 14, 16, 22 of the first pump 12, for determining the activation or exclusion timing of device 1;

the synchronization of the functioning of pistons 25 of first pump 12 with the cardiac rhythm of the treated patient, in case of use of device 1 for supporting the left heart ventricle VS;

the variation of the operative parameters (speed, phase, width etc.) of kinematic mechanisms 28 of the device 27 for operating pistons 25 of the first pump 12 for determining the speed, the quantity and the pressure of the blood inserted in the blood stream of the treated patient;

the synchronization of the working of pump 35 with the heart rhythm of the treated patient, in case of use of the device for assisting the left and/or right heart ventricle;

means for setting a nominal heartbeat in case of use of said device for assisting patients with cardiac fibrillation or cardiac arrest.

The first catheter 2 of the device 1 is introduced through the inguinal tract of the femoral artery AF of the treated patient by means of the introducer 10 with sealing elastic valve 11 and traced back into the blood circle of the patient until it reaches the aortic arch AO and in particular ascending aorta AA.

In standard operative conditions, the introduction of catheter 2 is performed with the help of X-ray equipments. In really emergency operative conditions the introduction of catheter 2 is performed with the help of ultrasound equipment or of optical probes temporarily inserted in the non-collapsible duct 5 of said catheter.

The extremal balloon 7 of catheter 2 is then placed in the ascending aorta AA so as not to further inferiorly interfere with the Sinus of Valsalva (not shown) and superiorly with the grafts of the supra-aortic trunks TS.

At the introduction, catheter 2 shows:
the duct 3 perfectly adherent to non-collapsible duct 5 due to its elasticity, except for a minimal portion external to the body of the treated patient, pre-loaded with blood compatible with the patient himself;
the non-collapsible duct 5 pre-loaded with blood compatible with the treated patient, similarly to the internal chambers 20 of pump 12;
the extremal balloon 7 in deflated condition.

Figure 3:
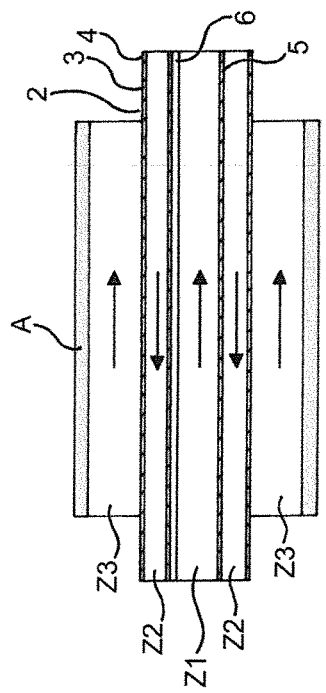

As shown in FIG. 3, at its introduction catheter 2 has a minimal transversal section that facilitates its backward ascending in the blood circle of the treated patient due to the adhesion of the elastic duct 3 to the non-collapsible duct 5 and to the deflated condition of extremal balloon 7.

The electronic control unit 36 provides for the start of device 27 for operating pistons 25 of pump 12 and to the synchronization of the pumping rhythm of said pistons 25 with the heart rhythm of the patient treated.

In this stage the electrovalves 14, 16 of ducts 13, 15 for the inlet and outlet of pump 12 are closed, while electrovalve 22 of the rigid median septum of the same is open.

Device 27 provides the alternate movement of pistons 25 and the consequent alternate movement of the operating liquid in the relative hydraulic cylinders 24 so as to produce the alternate passage of the blood between internal chambers 20 of pump 12 through electrovalve 22 of the median septum 21, due to the pressure of the elastic membranes 26 that keep separate the operating fluid contained in hydraulic cylinders 24 from the blood contained in the internal chambers 20 of pump 12. Once the synchronisation is obtained between the pumping rhythm of pistons 25 of pump 12 and the heart rhythm of the treated patient, the electronic control unit 36 provides for:

the inflating of extremal balloon 7 of catheter 2 through the second pump 35 connected to the capillary duct 6 of said catheter;
the opening of electrovalves 14, 16 of inlet and outlet ducts 13, 15 of pump 12,
the closing of electrovalve 22 of the median septum 21 of pump 12.

Through pistons 25 and in synchrony with the cardiac rhythm of the treated patient, pump 12 provides for:
the forced aspiration of the quantities of blood upstream of the extremal balloon 7 of catheter 2 and their routing towards the internal chambers 20 of pump 12 through the non-collapsible duct 5 of the catheter itself and inlet duct 13 of said pump,
the contemporary inlet of equivalent quantities of blood downstream of extremal balloon 7 of catheter 2, taken from internal chambers 20 of pump 12 through elastic duct 3 of said catheter and outlet duct 15 of said pump.

Figure 4:
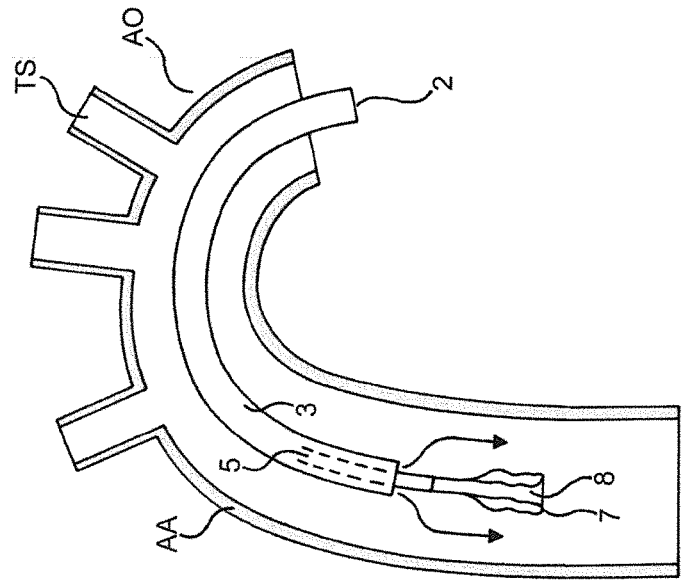

As shown in FIG. 4, when operating pistons 25 the blood flow introduced by pump 12 into elastic duct 3 of catheter 2 determines the expansion and consequently the maximum allowed transversal section thereof, limited by containment sleeve 4 that allows the optimal passage of the blood through said duct.

The aspiration and contemporary forced introduction of equivalent quantities of blood in the blood circle of the treated patient allows to assist or replace the functioning of the left heart ventricle VS of the patient and thus to obtain a regular blood flow with the pressure value managed by pump 12 and controlled by electronic control unit 36.

As shown in FIG. 4, when operating pistons 25 of pump 12 the aorta A of the treated patient results to be divided into:
an area Z1 for the passage of the blood aspired by pump 12, defined by the non-collapsible duct 5 of catheter 2;
an area Z2 of the passage of the blood inserted by pump 12, defined by the elastic duct of the catheter;
an area Z3 for the passage of the natural blood flow, defined by the space not occupied by the catheter 2 inside said aorta.

Figure 5:
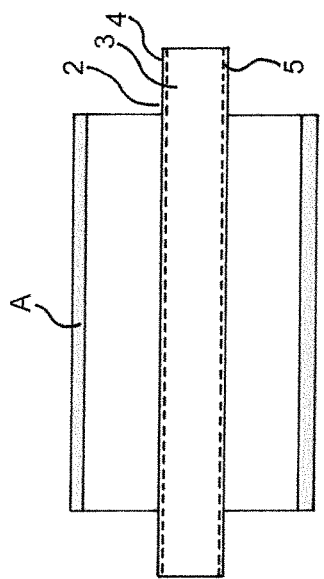

As shown in FIG. 5, the extremal balloon 7 of catheter 2 is provided with shaped loops 9 that allow the reflux of the blood introduced by pump 12 into the blood circle of the treated patient, from elastic duct 3 of catheter 2 to area Z3 for the passage of the natural blood flow of aorta A.

Figure 6:
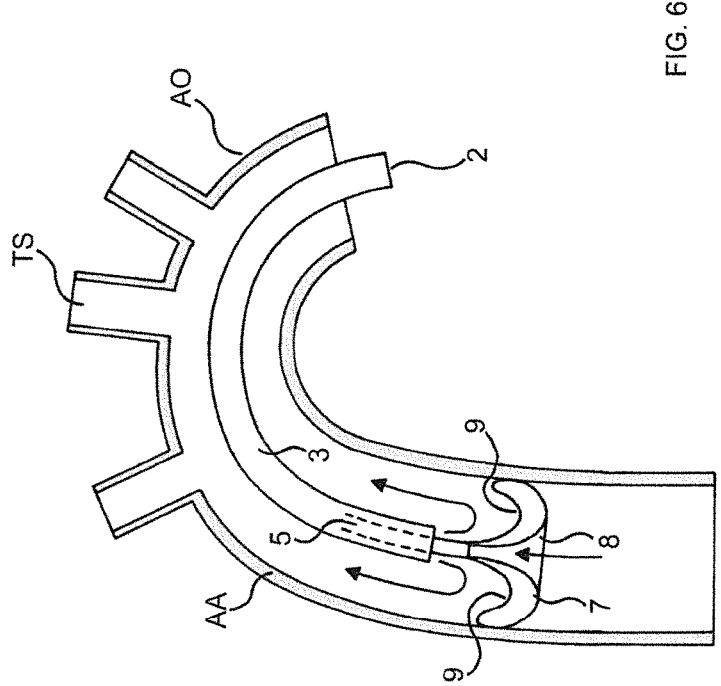

As shown in FIGS. 5 and 6, to avoid damages to aorta A of the patient treated potentially resulting from the pressure performed inside by extremal balloon 7 in its inflated condition, as well as to improve the general diastolic perfusion of the coronary vessels, the electronic control unit 36 further provides for:

the extremal balloon 7 to be in inflated condition during aspiration and the contemporary introduction of blood into the blood flow of the treated patient, due to pump 12 during the contraction phase of heart C of the patient himself;
the extremal balloon 7 to be in deflated condition during the end phase of blood introduction into the blood flow of the treated patient, due to pump 12 during the relaxing phase of heart C of the patient, so as to route the last part of the blood introduced with retrograde direction towards those points which previously were in contact with extremal balloon 7 and with original points of the coronary hosts, so as to determine the correct blood supply thereof.

When the treated patient has reached particular conditions (overcoming of acute heart crisis, satisfactory general conditions, minimal death risk) the electronic control unit 36 may determine a temporary disengagement of device 1, providing for:

the deflating of the extremal balloon 7 of catheter 2 through pump 35 connected to capillary duct 6 of said catheter;
the closing of electrovalves 14, 16 of inlet and outlet ducts 13, 15 of pump 12;
the opening of electrovalve 22 of the median septum 21 of pump 12.

The temporary disengagement of device 1 allows to restore the heart natural function of pumping blood and to maintain the catheter 2 in any case in place so as to assure a rapid ventricular assist in case of further heart failure in said patient.

As an alternative to pre-loading of device 1 with compatible blood it is possible to use said device directly with the treated patient's blood, that may be obtained:
- by taking the patient's blood before the application of the device 1 to said patient;
- by aspiration of the patient's blood through the non-collapsible duct 5 of catheter 2 with the help of the extraction of optical probes from the non-collapsible duct of said catheter, in this specific case acting as plungers of suction syringes;
- by the inlet of the patient's blood into non-collapsible duct 5 of catheter 2, during the introduction in place of said catheter.

As an alternative of the use of device 1 with compatible blood or directly with the blood of the treated patient, it is possible to use it with physiological solutions.

The use of device 1 with compatible blood, the patient's blood or physiological solutions is a choice of the health workers according to the conditions of the treated patient.

Detailed Functioning of Device 1 According to the Present Invention in Case of Use to Assist the Right Heart Ventricle The use of device 1 to assist the right heart ventricle VD may take place jointly or separately from its use to support the left heart ventricle VS of one and the same patient.

The use of device 1 to assist the right heart ventricle VD is particularly indicated in cases of total heart arrest or of problems or pulmonary blood circulation. In all other cases the value of blood pressure guaranteed by the use of said device 1 to assist the sole left heart ventricle VS is such as to assure an optimal blood circulation in the large systemic circle as well as in the small pulmonary circle of the treated patient.

The second catheter 32 of said device 1 is introduced in the inguinal tract of femoral vein VF of the treated patient by means of the same introducer 10 with elastic sealing valve 11 that may be used with the first catheter 2 or by means of a standard needle introducer, and it is traced back following the patient's blood circle until it reaches the area of the right heart ventricle VD comprised between the inferior vena cava CA and the superior vena cava CD.

In standard operative conditions the introduction of catheter 32 is performed with the help of X-ray equipment. In conditions of particular emergency the introduction of catheter 32 is performed with the help of ultrasound equipment. Extremal balloons 34 of catheter 32 are respectively placed between the right cardiac atrium AD and the first branch of the inferior vena cava CA (Azygos vein), and between the right cardiac atrium AD and the portion of the superior vena cava CD near the heart C of the treated patient.

The electronic control unit 36 provides for the synchronization of the pumping rhythm of the second pump 35 with the heart rhythm of the treated patient.

Once the synchronization between the pumping rhythm of pump 35 and the heart rhythm of the treated patient is obtained, the electronic control unit 36 cyclically provides for simultaneous inflating and deflating of both extremal balloons 34 of catheter 32, through said pump.

As shown in FIG. 8, the simultaneous inflating of both extremal balloons 34 determines their simultaneous expansion towards the right cardiac atrium AD, producing on the blood between them a pressure sufficient to determine the forced routing towards the right heart ventricle VD and the passage through it.

During ventricular contraction the pressure on the blood comprised between the extremal balloons 34 facilitates the right heart ventricle VD in pushing the blood towards the lungs of the treated patient, while in absence or deficit of ventricular contraction the pressure on the blood comprised between extremal balloons 34 replaces the pushing normally performed on the blood by the right heart ventricle VD.

The cyclical inflating and deflating of extremal balloons 34 of catheter 32 allows to assist or replace the working of the right heart ventricle VD of the treated patient and thus to obtain a regular blood flow passing through the right heart ventricle towards the lungs of the patient.

Even when it is used in support of the right heart ventricle, the device 1 bases its working on aspiration (corresponding to simultaneous deflating of both extremal balloons 34 of catheter 32) and on introduction (corresponding to simultaneous inflating of both extremal balloons 34 of catheter 32) of equivalent blood quantities into the blood circle of the treated patient, but with the features described in the following.

Under normal heart conditions the venae cavae CA, CD and the right cardiac atrium AD spontaneously and gradually fill up with blood.

In condition of heart failure the deflating of both extremal balloons 34 of catheter determines the forced aspiration into venae cavae CA, CD and into the right cardiac atrium AD of an amount of blood equivalent in volume to the quantity of blood introduced by pump 12 into the blood circle of the patient through elastic duct 3 of catheter 2.

The initial phase of simultaneous inflating of the extremal balloons 34 of catheter 32 determines the introduction into the right heart ventricle VD of the exact amount of blood required and under moderate pressure.

In normal working condition, the right heart ventricle VD empties completely during the previous contraction, requiring the exact amount of blood to be pushed towards the lungs. In condition of heart failure, the right heart ventricle VD empties only partially requiring a smaller amount of blood during its relaxation due to the stagnation inside.

The end phase of simultaneous inflating of extremal balloons 34 of catheter 32 pushes towards the lungs also said stagnation. The pressure on the blood comprised between the extremal balloons 34 of catheter 32 is such as to cause an effective forced advancement determining at the same time the opening of the tricuspid valve VT, the crossing of the right heart ventricle VD, the entering of the arterial cone and finally the arrival in the pulmonary artery.

Further Considerations on Device 1 According to the Present Invention

The device 1 according to the present description may be immediately applied to the infarcted patient, as the relative catheters 2, 32 and the pumps 12, 35 linked thereto produce a limited impact on the general clinical conditions of the patient. The impact of device 1 on the patient is limited also by the same application procedure that provides, first of all, the introduction of first catheter 2 which independently guarantees a relevant part of the natural blood circle, and secondly—and only where necessary—the joint introduction of the second catheter 32 which guarantees the remaining part of the natural blood circle.

However, device 1 requires the presence of a closed and continuous blood circle; therefore the use thereof is excluded in the extreme cases of rupture of the patient's blood vessels or of his heart.

Device 1 allows a rapid improvement of the general conditions of the patient to whom it has been applied and a consequent drastic reduction of his death risk, allowing him to be safely transported to hospital for heart treatment.

Device 1 may be applied to the patient with the sole help of ultrasound of optical equipment, which means also on board of ambulances etc., usually lacking X-ray equipment, because catheters 2, 32 of device 1 may be introduced and placed on site through large blood vessels easily recognizable even without X-ray equipment (femoral veins and arteries, inferior and superior vena cava). Furthermore, the ultrasound detectability of the distal ends of the catheters can be accentuated by their realization with eco-detectable materials or by the insertion of eco-detectable materials within them.

Device 1 may allow to perform diagnostic and/or therapeutic treatment interventions on the patient to whom it has been applied. This is made possible because the non-collapsible duct 5 of catheter 2 provides a comfortable and safe access to different kinds of diagnostic or operative probes.

In particular, device 1 allows to:
- perform, with mitigated risk for the patient, diagnostic operations of coronary angiography or similar;
- perform, with mitigated risk for the patient, operations of reparative coronary angioplasty, stent applications or similar;
- perform, with mitigated risk for the patient, reparative operations of bypass application or general surgery, reducing the use of heart-lung machines;
- perform, without waiting for the patient, operations normally unsustainable due to the extreme debilitation condition of the infarcted patient.

Should the patient have a negative reaction to an ongoing operation (with fibrillation or heart arrest) the device could maintain a correct blood circulation and thus give the time for performing the disengaging manoeuvres of the operations in progress and the restore or restart of the heart activity of the patient (defibrillation, stimulation etc.).

The latter consideration opens the way to potential new types of diagnostic or therapeutic treatments for the infarction patient.

The operating safety guaranteed by device 1 allows to speculate with efficient and safe diagnostic operations (coronary angiography performed in connection with device 1 which assures the blood circulation) which, in presence of partial coronary occlusions may be easily convertible into therapeutic interventions regardless of the application of stents and of the consequent lifelong assumption of anticoagulant and anti-rejection drugs.

The operating safety guaranteed by device 1 allows to speculate also with local healing interventions or treatments of the coronaries' internal tissues (performed through the non-collapsible duct 5 of catheter 2 of device 1) for gradually obtaining a perfect healing.

These new typologies of diagnostic or therapeutic treatment could allow the complete eradication of the "infarction pathology".

If the supposed new diagnostic interventions were performed like routine tests for patients at risk, they would allow the immediate performing of the supposed new therapeutic interventions, drastically reducing the negative effects and the death risk normally produced by heart attacks (at least in those Countries in which it is possible to guarantee similar types of diagnostic and therapeutic interventions).

The invention claimed is:

1. A device for ventricular emergency support of a treated patient, the device comprising:
    a first flexible catheter with a variable transversal section, the first catheter comprising:
        an elastic duct for an inlet of blood into a blood flow of the treated patient, the elastic duct being configured to vary an amplitude of a transversal section of the elastic duct in proportion to a quantity and to a pressure of the blood introduced in the blood flow of the treated patient; and
        a first extremal balloon configured for controlled occlusion of an ascending aorta of the treated patient, the first extremal balloon having, in an inflated condition, an umbrella-shaped form including shaped loops configured for a reflux of the blood inserted into the elastic duct in a natural direction of the blood flow of the treated patient;
    a first pump coupled to the first catheter for the aspiration and contemporary input of equivalent blood quantities into a blood circle of the treated patient;
    a second flexible catheter with a fixed transversal section, provided with at least two second extremal balloons, the second flexible catheter being spaced between the at least two second extremal balloons, for the controlled occlusion of the inferior vena cava and of the superior vena cava of the treated patient;
    a second pump coupled to the first and second catheter for inflating and deflating the first and second extremal balloons of the first and second catheter; and
    an electronic control unit for adjusting and controlling operational parameters of the first and second pump, and for detection of cardiac parameters of the treated patient.

2. The device according to claim 1, wherein the first catheter is configured to be inserted into a femoral artery of the treated patient and led up along the bloodstream until the first catheter has reached an aortic arch, in an initial condition of minimal transversal section, and wherein the first extremal balloon configured to be positioned near the ascending aorta of the treated patient, in a deflated condition.

3. The device according to claim 1, wherein the second catheter is configured to be inserted in an inguinal tract of a femoral vein of the treated patient and led up along the bloodstream until the second catheter reaches an area of a right cardiac ventricle comprised between an inferior vena cava and a superior vena cava, and wherein the second extremal balloons are configured to be placed between a right cardiac atrium and a first branch of the inferior vena cava of the treated patient, and between the right cardiac atrium and a portion of the superior vena cava adjacent to a heart of the treated patient, in a deflated condition.

4. The device according to claim 1, wherein the first catheter, the second catheter, the first extremal balloon and the second extremal balloons have smooth surfaces, without sharp edges, so as to avoid damages to tissues of the arterial or venous vessels of the treated patients.

5. The device according to claim 1, wherein the first catheter, the second catheter and the first pump are configured for limiting interferences with the blood circle and configured to limit a risk of outbreaks of thrombi or emboli in the treated patient.

6. The device according to claim 1, wherein the first catheter and the second catheter each include a proximal end coupled to the first pump, and a distal end out of a material suitable for allowing ultrasound detection or comprise fragments of the material.

7. The device according to claim 1, wherein the first catheter further comprises:
    a containment sleeve, integrated in the elastic duct, for defining a greatest amplitude reachable by the transversal section of the elastic duct;

a non-collapsible duct, internal to the elastic duct, for blood aspiration from the blood flow of the treated patient; and a capillary duct, internal to the non-collapsible duct for inflating and deflating the first extremal balloon, connected to the second pump.

8. The device according to claim 7, wherein the first catheter is configured to divide the aorta of the treated patient into:

an area for the passage of blood aspired by the blood flow of the treated patient, defined by the non-collapsible duct;

an area for the passage of blood inserted into the blood flow of the treated patient, defined by the elastic duct; and an area for the passage of natural blood flow, defined by the space not occupied by the first catheter inside the aorta of the treated patient.

9. The device according to claim 7, wherein the first extremal balloon comprises a light for the passage of the blood aspired by the non-collapsible duct of the first catheter.

10. The device according to claim 1, wherein the first pump comprises:

a Y-shaped inlet duct, for the inlet of the blood aspired from the blood flow of the treated patient, provided with an electrovalve connected to a non-collapsible duct of the first catheter;

a Y-shaped outlet duct, for the outlet of the blood inserted into the blood flow of the treated patient, provided with an electrovalve, connected to the elastic duct of the first catheter;

a machine body containing two internal chambers, separated by a rigid median septum provided with an electrovalve, connected to the inlet and outlet ducts by unidirectional valves, working by difference of pressure, imposing to the blood entering and leaving the two internal chambers to always move in a same direction;

hydraulic cylinders with relative pistons that cyclically manage compression and expansion of an operating fluid that is kept separate from the blood contained in the two internal chambers by elastic membranes; and an electromechanical mechanism for operating pistons of the hydraulic cylinders, provided with eccentric kinematic mechanism coupled to a frame integral with the pistons and linearly sliding on guides with a stroke limited by cushioning springs.

11. The device according to claim 10, wherein the first pump is configured to determine:

a forced aspiration of blood quantities upstream of the first extremal balloon of the first catheter in an inflated condition, and routing of the blood quantities towards the internal chambers of the first pump through the non-collapsible duct of the first catheter and the inlet duct of the first pump, the inlet duct being in fluid communication with the non-collapsible duct of the first catheter;

a contemporary insertion of equivalent quantities of blood downstream of the first extremal balloon of the first catheter when in the inflated condition taken from the two internal chambers by the elastic duct of the first catheter and the outlet duct of the first pump, the outlet duct being in fluid communication with the elastic duct of the first catheter;

so as to produce equivalent blood flows aspired and forcedly inserted into the blood flow of the treated patient, for assisting or replacing a functioning of the left cardiac ventricle of the treated patient.

12. The device according to claim 10, wherein the electronic control unit is configured to:

control the electrovalves of the first pump, to manage the activation, exclusion or temporary disengagement of the device;

control of the second pump that allows the inflating and deflating of the first extremal balloon of the first catheter;

synchronize a pumping rhythm of pistons of first pump with the cardiac rhythm of the treated patient;

control of the operational parameters of kinematic mechanisms of the device for operating pistons of the first pump that allows the managing of the speed and/or quantity and/or of the pressure of the blood inserted in the blood stream of the treated patient;

synchronize the pumping of the second pump with the cardiac rhythm of the treated patient;

control the second pump, that allow the contemporary inflating and deflating of the second extremal balloons of the second catheter; and set a nominal heartbeat in case of use of the device on patients with cardiac fibrillation or cardiac arrest.

13. The device according to claim 1, wherein the second catheter comprises a non-collapsible duct for inflating and deflating the second extremal balloons, connected to the second pump.

14. The device according to claim 1, wherein the second extremal balloons have a spherical shape in a deflated condition.

15. The device according to claim 1, wherein the second pump is configured to determine:

a contemporary inflating of the second extremal balloons and a consequent thrust of blood contained in the right cardiac atrium creating a pressure that causes a forced passage thereof into the right cardiac ventricle; and a contemporary deflating of the second extremal balloons and a consequent production of a depression that causes a recall of peripheral blood and a refill of blood in the right cardiac atrium; and wherein the second pump is configured to produce blood flows forcedly aspired from the peripheral blood stream of the treated patient and forcedly inserted into the right cardiac atrium of the treated patient to assist or replace a functioning of the right cardiac ventricle.

16. The device according to claim 1, wherein the device further comprises at least one needle introducer for inserting the first catheter into the femoral artery of the treated patient, or of the second catheter into the femoral vein of the patient.

17. The device according to claim 16, wherein the needle introducer comprises an elastic valve that automatically adapts to the variable transversal section of the first catheter or to the fixed transversal section of the second catheter for avoiding blood leaks from the femoral artery or from the femoral vein of the treated patient.

18. A device for ventricular emergency support of a treated patient, the device comprising:

a first flexible catheter with a variable transversal section, the first catheter including a first extremal balloon configured for controlled occlusion of an ascending aorta of the treated patient;

a first pump coupled to the first catheter for the aspiration and contemporary input of equivalent blood quantities into a blood circle of the treated patient, the first pump comprising:

a Y-shaped inlet duct, for the inlet of the blood aspired from the blood flow of the treated patient, provided with an electrovalve connected to a non-collapsible duct of the first catheter;

a Y-shaped outlet duct, for the outlet of the blood inserted into the blood flow of the treated patient, provided with an electrovalve, connected to an elastic duct of the first catheter;

a machine body containing two internal chambers, separated by a rigid median septum provided with an electrovalve, connected to the inlet and outlet ducts by unidirectional valves, working by difference of pressure, imposing to the blood entering and leaving the two internal chambers to always move in a same direction;

hydraulic cylinders with relative pistons that cyclically manage compression and expansion of an operating fluid that is kept separate from the blood contained in the two internal chambers by elastic membranes; and an electromechanical mechanism for operating pistons of the hydraulic cylinders, provided with eccentric kinematic mechanism coupled to a frame integral with the pistons and linearly sliding on guides with a stroke limited by cushioning springs;

a second flexible catheter with a fixed transversal section, provided with at least two second extremal balloons, the second flexible catheter being spaced between the at least two second extremal balloons, for the controlled occlusion of the inferior vena cava and of the superior vena cava of the treated patient;

a second pump coupled to the first and second catheter for inflating and deflating the first and second extremal balloons of the first and second catheter; and an electronic control unit for adjusting and controlling operational parameters of the first and second pump, and for detection of cardiac parameters of the treated patient.

19. The device according to claim 18, wherein the first pump is configured to determine:

a forced aspiration of blood quantities upstream of the first extremal balloon of the first catheter in an inflated condition, and routing of the blood quantities towards the internal chambers of the first pump through the non-collapsible duct of the first catheter and the inlet duct of the first pump, the inlet duct being in fluid communication with the non-collapsible duct of the first catheter;

a contemporary insertion of equivalent quantities of blood downstream of the first extremal balloon of the first catheter when in the inflated condition taken from the two internal chambers by the elastic duct of the first catheter and the outlet duct of the first pump, the outlet duct being in fluid communication with the elastic duct of the first catheter;

so as to produce equivalent blood flows aspired and forcedly inserted into the blood flow of the treated patient, for assisting or replacing a functioning of the left cardiac ventricle of the treated patient.

20. The device according to claim 18, wherein the elastic duct of the first catheter is an inlet for blood into a blood flow of the treated patient, the elastic duct being configured to vary an amplitude of a transversal section of the elastic duct in proportion to a quantity and to a pressure of the blood introduced in the blood flow of the treated patient, and wherein the first extremal balloon has, in an inflated condition, an umbrella-shaped form including shaped loops configured for a reflux of the blood inserted into the elastic duct in a natural direction of the blood flow of the treated patient.

* * * * *